ns on the Primary in Vitro Immune Response *Journal of Immun.*, 1975, vol. 115, pp. 575–578.

United States Patent [19]

Braude

[11] 4,376,822
[45] Mar. 15, 1983

[54] PRODUCTION OF HUMAN IFN-γ (IMMUNE) INTERFERON

[75] Inventor: Irwin A. Braude, Burke, Va.

[73] Assignee: Meloy Laboratories, Inc., Springfield, Va.

[21] Appl. No.: 255,139

[22] Filed: Apr. 17, 1981

[51] Int. Cl.$^3$ .......................... C12P 21/00; C12N 5/00
[52] U.S. Cl. ....................................... 435/68; 435/240; 435/811
[58] Field of Search .................. 435/68, 240, 241, 811

[56] References Cited

PUBLICATIONS

Vilcek et al., in Yip et al., Stimulation of Human Gamma Interferon Production by Diterpene Esters *J. of Immun.*, 1981, pp. 131–139, vol. 34, Ref. 32.
Langford et al., Biological Effects of SEA on Human Peripheral Lymphocytes *J. of Immun.*, 1978, vol. 22, pp. 62–68.
Smith et al., The Effects of Staphylococcal Enterotoxins on the Primary in Vitro Immune Response *Journal of Immun.*, 1975, vol. 115, pp. 575–578.
Epstein, The Effects of Interferons on the Immune Response in Vitro and in Vivo *Interf. and Therhetions*, 1977, CRC Press, Cleveland, pp. 114–121.

*Primary Examiner*—Thomas G. Wiseman
*Assistant Examiner*—Kathleen S. McCowin

[57] ABSTRACT

A process is disclosed for producing human immune interferon with cell cultures of human peripheral blood leukocytes modulated with Mezerein or 12,13 phorbol dibutyrate and induced with *Staphylococcal aureus* enterotoxin B. After cultures are incubated for 3 to 7 days crude interferon on the order of $10^3$ units of interferon/ml. is produced.

13 Claims, No Drawings

PRODUCTION OF HUMAN IFN-γ (IMMUNE) INTERFERON

BACKGROUND OF THE INVENTION

(1) Field of the Invention

This invention relates to the production of human immune interferon. More particularly, the invention relates to a process for the production of human immune interferon from human peripheral blood leukocytes modulated with Mezerein or 12, 13 phorbol dibutyrate and induced by *Staphylococcal aureus* enterotoxin B.

(2) The Prior Art

Interferon was discovered by Isaacs and Lindenmann in 1957, who observed that fluids from virus-infected cell cultures contained a protein which could react with normal cells to render them resistant to infection by a wide variety of viruses. Since then, considerable work on producing leukocyte interferon has been done by Dr. Kari Cantell in Finland, see "Production and Preparation of Human Leukocyte Interferon", K. E. Mogensen and K. Cantell, *Pharmac Ther. C.* Vol. 1, pp. 369-381, 1977. In addition to potent antiviral effects, interferon possesses anticellular, immunoregulatory, and antitumor activities. Consequently, the use of human interferon in the treatment of cancer and viral infections in man has raised considerable interest.

Interferons are classified into three major species designated IFN-α (leukocyte), IFN-β (fibroblast) IFN-γ (immune). Leukocyte and fibroblast interferons are induced by viruses or synthetic polynucleotides. Immune type interferons are usually induced in primed lymphocytes by a specific antigen or in unprimed lymphocytes by T-cell mitogens.

The present invention teaches a process for producing human immune interferon (IFN-γ) which is efficient and functional. A variety of procedures have been described for producing immune interferon from peripheral blood leukocytes. Some of the most popular systems employ the use of Concanavalin A, Phytohemagglutinin A, and *Staphylococcal aureus* enterotoxin A. One such process is described by Jan Vilcek et al. in the article, "Characteristics of Interferons Produced in Cultures of Human Lymphocytes by Stimulation with *Carynebacterium parvum* and Phytohemagglutinin" appearing in *Biochemical Characterization of Lymphokines,* p. 323, Academic Press.

SUMMARY OF THE INVENTION

Generally, the invention provides a process for the production of human immune interferon. The present process involves the production of heterogeneous human immune interferon from human peripheral blood leukocytes by first modulating a viable cell suspension with a modulator of either Mezerein or 12, 13 phorbol dibutyrate and inducing with *Staphylococcal aureus* enterotoxin B. Modulated cells induced with *Staphylococcus aureus* enterotoxin B, a microbial toxin produced by *Staphylococcus aureus,* facilitates immune interferon production to a greater extent than such prior art immune interferon inducers as Phytohemagglutinin and Concanavalin A. Moreover, *Staphylococcal aureus* enterotoxin B is effective in stimulating immune interferon production over a wide concentration range.

It is the general object of this invention to provide a process for production of human immune interferon which is efficient and functional. Consequently, this process for producing human immune interferon offers a feasible approach to preparing commercial quantities of crude immune interferon which may be purified for physiochemical characterization, structure studies, antibody production, and clinical application. It is also the object of this invention to provide a process for producing human immune interferon mRNA which may then be used to produce its cDNA for subsequent cloning.

Other objects, features and advantages will be evident from the following detailed description of the invention.

DETAILED DESCRIPTION OF PREFERRED EMBODIMENTS

In accordance with the preferred embodiments of this invention, human peripheral blood leukocytes are provided as a viable cell source for human immune interferon production. Human peripheral blood leukocytes may be obtained by a variety of standard clinical techniques, such as lymphocytes obtained from buffy coats or by leukophoresis on a hemonetics machine.

One suitable method involves collecting whole blood (usually 100 ml volumes) by venipucture from healthy donors in acid-citrate-dextrose solution or in heparinized containers. The acid-citrate and heparin are normal additives to blood units preventing coagulation of the blood cells upon standing. The whole blood is centrifuged and the plasma fraction removed. The material remaining (red blood cells and white blood cells) contains the peripheral blood lymphocytes.

Another method of isolating the peripheral blood lymphocytes is by the Ficoll-Hypaque gradient method as described in A. Boyum, "Isolation of Leukocytes from Human Blood", 21 *Scand. J. Clin. Lab Invest.* Suppl. 31-50 (1968). A substantial portion of the cells derived from this technique will be lymphocytes, of which the T-cell originated lymphocytes will dominate. The remaining monocytic leukocyte cells will be B-cell lymphocytes, monocytes and null cells.

The red blood cells are lysed and removed from the preparations by treatment with buffered ammonium chloride at approximately 7-10 volumes of 0.83% ammonium chloride (weight/volume, w/v). Lysed material is immediately centrifuged to collect the sedimented white blood cells. When processed on a small scale centrifuging batch-wise at approximately 25×g for about 10 minutes at about 4° C. is adequate. Processing cells on a large scale is conveniently accomplished using continuous flow centrification. The supernatant contains cell lysates and debris and the pellet contains the sedimented leukocyte.

The leukocytic cells are resuspended in culture media, with about $1.0 \times 10^6$ to about $9.0 \times 10^6$ cells/ml as the preferred concentration and from about $4.0 \times 10^6$ to about $7.0 \times 10^6$ cells/ml as the optimum concentration. A commercially available culture media which has been found to be especially suitable is RPMI 1640 (Gibco).

In some cases it may be desirable to add antibiotics to the cell suspension to prevent contaminating bacterial growth. Broad spectrum antibiotics such as 100 U of penicilli per ml cell suspension, 100 μg of streptomycin per ml cell suspension, or 100 μg of gentamicin per ml cell suspension may be used. Although the inclusion of antibiotics in the cell suspension inhibits bacterial growth, the antibiotics themselves are contaminants in the sense that they must be removed from the crude interferon. Even trace amounts of antibiotics if not completely removed from the interferon product may cause allergic reactions when administered to susceptible patients.

To the culture media containing the resuspended leukocyte cells is added a modulator selected from the group consisting of Mezerein and 12, 13 phorbol dibutyrate. These modulators are commercially available from CCR, Inc., Eden Prairie, Minn. The modulator is added in an amount of about 0.7 to about 60 ηg/ml of cell suspension, preferably about 1 to about 10 ηg/ml of cell suspension. To the modulated cell suspension the inducer *Staphylococcus aureus* enterotoxin B is added either cocurrently or following incubation. The cell suspension containing the modulator, when incubation if desired, is incubated up to about 3 hours while slowly stirring. By incubation it is meant that the suspension is maintained at a temperature of about 37° C. Although SEB alone will induce cells to produce human immune interferon (IFN-γ), the addition of a modulator by a mechanism which is not entirely understood, increases the number of cells capable of responding to SEB and thus enhancing the yields. It is preferable to add the modulator prior to adding the inducer.

Following incubation of the modulated cell suspension, *Staphylococcus aureus* enterotoxin B is admixed into the viable cell suspension. Applicant has demonstrated that *Staphylococcus aureus* enterotoxin B (SEB), as compared to well-known immune interferon inducers, *Staphylococcus aureus* enterotoxin A, Phytohemagglutinin-A and Concanavalin A, stimulates production of higher immune interferon titer and to produce this high concentration over a wide concentration range. A range of from about 0.01 to about 10.0 μg SEB/ml cell suspension is used. *Staphylococcal aureus* enterotoxin B, although active over a wide concentration range, is preferably added to the cell suspension at a final concentration of about 0.1 to about 2.0 μg Inducer/ml of modulated cell suspension.

It has also been found that interferon yield is further increased if a nutrient source such as a protein source, for example fetal calf serum (fetal calf serum lacks bovine lymphocytes which, if present, would produce bovine immune interferon) is added to the cell suspension at a final concentration of about 3% to about 15%, preferably from about 4 to about 10% (volume/volume, v/v) serum modulated cell suspension. While it is preferable to add the fetal calf serum following the addition of SEB, it should be understood that the addition of fetal calf serum may be added at any point in the process.

After mixing *Staphylococcal aureus* enterotoxin B with the viable cell suspension containing the human peripheral lymphocytes the culture is then incubated. Cultures of the cell suspension and inducers are incubated for about 2 to about 7 days, the optimum incubation being about 3 to 5 days, at 37° C. The culture is gently stirred, desirably at a rate of about 10 rpm, to maintain the suspended material in suspension and to provide adequate suspension-surface to air contact for metabolic equilibration. After about 3 days incubation the cumulative production of interferon diminishes.

The appropriate amount of mixture to be included in a culture container is determined by the capacity of that particular container such that a suitable volume of air makes contact with the cell suspension to maintain viability over an incubation period. Conditions must be such that a dynamic exchange of $CO_2$ and other volatile metabolites of the cell suspension can be established between the suspension media and the air volume. Suitably, 36-liter bottles are seeded with 18 to 22 liters of cell suspension under a $CO_2$ blanket. The system is buffered to a pH of about 7.0 to about 7.6, preferably about 7.2 to about 7.4.

After the cell culture suspension has incubated for the desired period of time sufficient to produce extractable yields of crude immune interferon, the cells are removed by centrifugation at 2620×g, for 60 minutes, at 4° C. Extractable yields of crude immune interferon may result from crude cell suspensions containing more than 1000 units interferon activity/ml cell suspension. The residual cells can later be used for leukocyte interferon production using a viral inducer or reinduction of IFN-γ using a mitogen. The supernatant containing the crude human immune interferon is stored at 4° C. until further processing. The crude human immune interferon would not be expected to be used as is but would be purified.

A purification process is described in the paper entitled, "Partial Purification and Characterization of Human γ (immune) Interferon", 78 *Proc. Natl. Acad. Sci. U.S.A.* No. 3 (1981).

Another technique for purifying human IFN-γ (immune) interferon is to take the supernatant material and subject it to a concentration and purification step involving the adsorption of interferon onto Controlled Pore Glass beads. Controlled Pore Glass beads are composed of borosilica glass varying in mesh and bead size. Commercially available sources for controlled glass beads include Corning and Electro-Nucleonics, Inc. Those Beads provided by Electro-Nucleonics, Inc. are available in three mesh sizes (80/120; 120/120; 200/400) and eleven pore sizes (75 to 3000 Angstroms). Although the beads are produced for exclusion or gel filtration-type chromatography, the present process uses the beads for adsorption chromatography. Adsorption characteristics are generally a function of chemical composition rather than physical composition. Crude human IFN-γ (immune) interferon preparations are loaded onto columns containing Controll Pore Glass beads. The column is then washed with low salt concentration and the interferon is diluted with high salt concentrations.

The preferred embodiments of this invention are further illustrated by the examples which follow. In the examples, the following material was employed:

*Staphylococcal aureus* enterotoxin B was produced and purified by the Life Sciences Division of Meloy Laboratories, Inc., Springfield, Va.

Samples of Tables I and II were titrated in a semi-micro c.p.e.-inhibition assay using WISH cells as the indicator cells and Vesicular Stomatitis Virus (VSV) as the challenge virus.

EXAMPLE 1

The red blood cells of leukocytes obtained from buffy coats were lysed with 7 volumes of 0.83% (weight-/volume) buffered ammonium chloride and immediately centrifuged at approximately 25×g for 20 minutes to separate the lysed red blood cells in the supernatant from the pellet containing the leukocytes. These cells were suspended to about $5.0\times10^6$ cells per ml in RPMI 1640 medium (Gibco) to form a culture.

Mezerein, the modulator, was added to the culture at about 7 μg/ml of culture and mixed. The mixture was incubated at 37° C. for two hours under gentle stirring. Following incubation, Staphylococcal enterotoxin B (SEB), the inducer, was added at a final concentration of 1.0 μg/ml. To the induced mixture, fetal calf serum was added until the fetal calf serum in the mixture reached 10%.

The cultures were then incubated for about 72 hours at 37° C. in a gently stirred container. After incubation the cultures (crude immune interferon) were harvested by centrifugation at 2620×g at 4° C. for 60 minutes. The supernatant containing crude interferon was separated from the cells and particulate material. The interferon yield was approximately $10^3$ units/ml. Using the process of this invention, modulated SEB induces approximately 2 to 3 times more immune interferon than SEB alone.

EXAMPLE 2

The effects of modulation on interferon production in human leukocytes induced by Staphylococcal Enterotoxin B (SEB) at a concentration of 1 μg/ml. is shown in Table I. The general procedure of Example I was used.

TABLE I

| | Interferon Titer, Units/ml |
|---|---|
| Amount Mezerein added, ηg/ml | |
| 0.5 | 120 |
| 0.75 | <30 |
| 1.0 | 60 |
| 3.0 | 180 |
| 5.0 | 1272 |
| 7.0 | 1440 |
| 9.0 | 720 |
| 50.0 | 2304 |
| 12,13 Phorbol dibutyrate added, ηg/ml | |
| 0.5 | 36 |
| 5.0 | 144 |
| 50.0 | 144 |

The preferred production of immune interferon in SEB induced cultures occurred at an additional level above about 1 μg/ml. cell suspension.

EXAMPLE 3

The effects of various dosages of inducer, SEB, on interferon production in human leukocytes modulated by Mezerein at a level of 7 ηg/ml of cell suspension is shown in Table II. Unless indicated otherwise the procedure of Example I was used.

TABLE II

| Amount of SEB added, μg/ml | Interferon Titer, Units ml |
|---|---|
| 0.001 | 180 |
| 0.005 | 180 |
| 0.01 | 180 |
| 0.1 | 960 |
| 0.5 | 960 |
| 1.0 | 720 |

The optimum production of immune interferon in modulated cultures occurred at an addition level above about 1.0 μg/ml.

EXAMPLE 4

The interferon production in human peripheral lymphocytes modulated by Mezerein and induced by Staphylococcal enterotoxin B (SEB) was compared to the interferon production induced by optimum concentrations of Staphylococcal enterotoxin A (without a modulator), Phytohemagglutinin-P (PHA-P) and concanavalin A (Con A). Leukocyte cultures ($5 \times 10^6$ cells/ml RPMI medium) were stimulated with optimal doses of SEB, SEA, PHA-P and Con A. Modulated SEB induced about 2 to 4 times, 5 to 10 times, and 10 to 20 times more immune interferon than unmodulated SEA, unmodulated PHA-P or unmodulated Con A, respectively.

All of the detectable interferon is immune in this system. Treatment at pH 2 resulted in 99% loss of activity in 1 hour, whereas control leukocyte interferon is only slightly affected. Antibody to human leukocyte interferon had no effect on immune interferon, whereas completely neutralizing the antiviral effect of leukocyte interferon. Furthermore, the immune interferon is not active on bovine cells and demonstrates a different chromatographic profile when compared to leukocyte interferon.

Finally, there has been presented here a process for the production of human immune interferon which is as efficient, functional, and less costly than those currently used to produce human immune interferon for clinical trials in viral infections and cancers.

While the invention has been described in terms of preferred embodiments constituting the best mode known to the applicants at the time of this application, various changes may be made in the invention without departing from the scope thereof, which is defined by the following claims.

What is claimed is:

1. A process for the production of human immune interferon comprising:
    (a) providing a viable cell suspension of RPMI 1640 culture medium containing approximately $1.0 \times 10^6$ to about $9.0 \times 10^6$ human peripheral blood leukocytes per ml;
    (b) adding a modulator selected from the group consisting of mezerein and 12, 13 phorbol dibutyrate to said cell suspension in an amount of at least 0.7 ηg/ml. of said cell suspension;
    (c) mixing said modulator in said cell suspension to form a mixture;
    (d) incubating said mixture under physiological conditions for a period of time sufficient to thoroughly stimulate the cells;
    (e) mixing *Staphylococcal aureus* enterotoxin B into said modulated mixture such that a final amount ranging from about 0.01 to about 10.0 μg/ml. of modulater cell suspension is achieved;
    (f) incubating said modulated mixture under physiological conditions for a period of time sufficient to produce extractable yields of human immune interferon; and
    (g) separating after incubation the cellular material of the cell suspension from the soluble fraction of the mixture, said soluble fraction containing a substantial portion of the produced human immune interferon and soluble contaminants.

2. The process in accordance with claim 1, wherein the cell suspension contains approximately $4.0 \times 10^6$ to about $7.0 \times 10^6$ cells per ml.

3. The process in accordance with claim 2, wherein the modulator is mezerein.

4. The process in accordance with claim 2, wherein the modulator is 12, 13 phorbol dibutyrate.

5. The process according to claims 3 or 4, wherein the modulated mixture is incubated for up to about 3 hours.

6. The process in accordance with claim 3 or 4, wherein said modulator is added in an amount of between about 1 and about 10 ηg/ml. cell suspension.

7. The process in accordance with claim 3, wherein said inducer results in a final concentration within said mixture ranging from about 0.1 to about 2.0 μg of inducer/ml. of modulated cell suspension.

8. The process in accordance with claim 3 or 4, wherein the induced mixture is incubated from about 2 days to about 7 days.

9. The process in accordance with claim 8, wherein the induced mixture is incubated from about 3 days to about 5 days.

10. The process in accordance with claim 1, wherein fetal calf serum is added to the mixture in an amount which results in a concentration of fetal calf serum in said mixture of from about 3% to about 15%.

11. The process according to claim 10, wherein fetal calf serum is added to the induced mixture in an amount which results in a concentration of fetal calf serum in said mixture of from about 4% to about 10%.

12. The process in accordance with claim 1, wherein the human immune interferon is purified from the contaminants.

13. A process for the production of human interferon comprising:

(a) providing a viable cell suspension of RPMI 1640 culture medium containing approximately $1.0\times10^6$ to about $9.0\times10^6$ human peripheral lymphocytes per ml;

(b) adding mezerein as a modulator to the cell suspension in an amount of at 0.7 ηg/ml. of cell suspension;

(c) mixing said modulator in said cell suspension to form a mixture;

(d) incubating said mixture under physiological condition for up to about 3 hours;

(e) providing the inducer *Staphylococcal aureus* enterotoxin B;

(f) mixing said inducer in said modulated cell suspension within a container to form an induced mixture wherein said inducer results in a final concentration within said mixture ranging from about 0.01 to about 10.0 μg of inducer/ml of modulated cell suspension;

(g) adding fetal calf serum to the mixture in an amount which results in a concentration of fetal calf serum in said mixture of from about 3% to about 15%;

(h) incubating said induced mixture under physiological conditions from about 3 to about 7 days;

(i) separating after incubation the cellular material of the cell suspension from the soluble fraction of the mixture; said soluble fraction containing a substantial portion of the produced human immune interferon and soluble contaminants; and (j) purifying the human immune interferon from the contaminants.

* * * * *